(12) United States Patent
Okabe et al.

(10) Patent No.: US 7,939,706 B2
(45) Date of Patent: May 10, 2011

(54) AUTOMATIC URINE DISPOSAL DEVICE AND URINE RECEPTACLE USED THEREFOR

(75) Inventors: Kenichi Okabe, Chiyoda (JP); Junichi Kobayashi, Ushiku (JP); Shigeru Machida, Iwama (JP); Ryousuke Miyagawa, Kasukabe (JP); Yoshikazu Ishitsuka, Minori (JP); Ichiro Wada, Toyohama (JP); Miou Suzuki, Toyohama (JP)

(73) Assignees: Hitachi, Ltd., Tokyo (JP); Uni-Charm Corporation, Ehime-Ken (JP)

( * ) Notice: Subject to any disclaimer, the term of this patent is extended or adjusted under 35 U.S.C. 154(b) by 629 days.

(21) Appl. No.: 11/869,843

(22) Filed: Oct. 10, 2007

(65) Prior Publication Data
US 2008/0033386 A1 Feb. 7, 2008

Related U.S. Application Data

(62) Division of application No. 10/954,001, filed on Sep. 30, 2004, now abandoned.

(30) Foreign Application Priority Data

Sep. 30, 2003 (JP) ................................ 2003-340488

(51) Int. Cl.
*A61F 13/15* (2006.01)
*A61F 13/20* (2006.01)

(52) U.S. Cl. .................. 604/361; 604/317; 604/318
(58) Field of Classification Search .................. 604/317, 604/319, 361
See application file for complete search history.

(56) References Cited

U.S. PATENT DOCUMENTS

| 4,072,151 | A | 2/1978 | Levine |
| 4,323,069 | A * | 4/1982 | Ahr et al. ...................... 604/378 |
| 4,631,061 | A | 12/1986 | Martin |
| 4,747,166 | A * | 5/1988 | Kuntz ............................ 4/144.1 |
| 5,648,142 | A | 7/1997 | Phillips |
| 5,911,222 | A | 6/1999 | Lawrence et al. |
| 6,039,060 | A | 3/2000 | Rower |
| 2001/0037097 | A1 | 11/2001 | Cheng |

FOREIGN PATENT DOCUMENTS

| WO | WO 93/09736 | 5/1993 |
| WO | WO 02/090106 A1 | 11/2002 |

* cited by examiner

*Primary Examiner* — Melanie J Hand
(74) *Attorney, Agent, or Firm* — Antonelli, Terry, Stout & Kraus, LLP.

(57) ABSTRACT

In a urine receptacle of an automatic urine disposal device, a urine backflow prevention sheet, with no water permeability, having funnel-shaped pores, is placed between a top sheet and a urine absorbing sheet. A pair of rectangular electrodes, constituting a urine detection sensor, is glued onto an electrode support sheet and is placed between the top sheet and the urine backflow prevention sheet. A plurality of funnel-shaped pores is formed on the urine backflow prevention sheet.

9 Claims, 5 Drawing Sheets

AUTOMATIC URINE DISPOSAL DEVICE AND URINE RECEPTACLE USED THEREFOR

CROSS-REFERENCE TO RELATED APPLICATION

This application is a divisional application of U.S. application Ser. No. 10/954,001, filed Sep. 30, 2004, now abandoned the contents of which are incorporated herein by reference.

The present application claims priority from Japanese application JP2003-340488 filed on Sep. 30, 2003, the content of which is hereby incorporated by reference into this application.

BACKGROUND OF THE INVENTION

The present invention relates to an automatic urine disposal device and a urine receptacle used for that purpose worn by the elderly with difficulty walking, hospitalized patients, physically disabled people, and others who are unable to voluntarily control the bladder or to clean up urine on their own.

In general, elderly, physically disabled people, and those who are hospitalized due to injuries or illness sometimes become unable to voluntarily control the bladder or clean up urine on their own. In those situations, generally, a catheter is directly inserted into the bladder to discharge urine or a paper diaper is used.

When a catheter is directly inserted into the bladder, the wearer feels great discomfort and there is also the probability of injuring the urethra or bladder or the occurrence of an infection. Thus, expertise as well as the use of special sterilized utensils is required.

Prolonged use of a paper diaper may cause urine leakage, feeling of discomfort, humidity inside the diaper, or skin troubles such as rashes. To avoid this, the paper diaper must be frequently changed, which will impose considerable physical and mental burdens on both the wearer and the caretaker. Imposed on a daily basis, those physical and mental burdens become a big concern and a significant economical burden as well.

In order to solve the problems listed above, an automatic urine disposal device, which uses a urine receptacle and a vacuum pump to suction urine and then to direct the urine into a urine tank via a urine drainage tube, has been developed. A urine detection sensor for detecting urination and activating the vacuum pump is used in such an automatic urine disposal device. As for the urine detection sensor, there are various methods available for urine detection such as: detection based on electric conduction of a pair of electrodes as a result of urination; detection based on changes in pressure inside the urine drainage tube as a result of urination; and detection based on detection of odor components in excretory substances. Detection based on changes in pressure inside the urine drainage tube as a result of urination and detection based on detection of odor components in excretory substances will make the device complicated and thus expensive. Therefore, for practical use, urine detection based on electric conduction of a pair of electrodes has been considered effective.

Automatic urine disposal devices with a urine detection sensor using a pair of electrodes have been disclosed in Japanese Application Patent Laid-open Publications No. Hei 07-171182 and No. Hei 10-85275.

The urine receptacle of an automatic urine disposal device has a urine absorbing sheet below a top sheet made of a nonwoven fabric which lets urine easily pass. A pair of electrodes, constituting a urine detection sensor, is located between the top sheet and urine absorbing sheet. Below the urine absorbing sheet, urine absorbing space forming material for defining a urine flow path is provided in order to collect urine from a large area. Sometimes the urine absorbing sheet or the urine absorbing space forming material fails to collect urine and the urine there remains uncollected. This may cause the uncollected urine to ooze toward the urine detection sensor when the wearer changes his/her posture or when his/her weight is shifted.

The urine detection sensor with a pair of electrodes becomes electrically conductive due to the residual urine oozing out, detects presence of urine, and activates the vacuum pump. If the vacuum pump becomes activated in this manner when the wearer is not urinating, the wearer feels discomfort, thus creating a problem that he/she cannot use it comfortably.

BRIEF SUMMARY OF THE INVENTION

The objective of the present invention is to provide an automatic urine disposal device which is able to prevent improper operation of a vacuum pump caused by residual urine even though a urine detection sensor with a pair of electrodes is used, and also to provide a urine receptacle to be used for such an automatic urine disposal device.

The present invention is characterized in that: a urine backflow prevention sheet having no water permeability with funnel-shaped pores is placed between a top sheet and urine absorbing sheet; and a pair of electrodes constituting a urine detection sensor is paced between the top sheet and the urine backflow prevention sheet. A plurality of funnel-shaped pores is formed on the urine backflow prevention sheet.

In the present invention, the urine detection sensor is placed on the urine backflow prevention sheet (on the top sheet side) with a plurality of funnel-shaped pores. Discharged urine can easily flow from the top sheet to a urine absorbing sheet since each funnel-shaped pore has a large opening area, and discharged urine cannot backflow easily as each funnel-shaped pore has a small opening area. This is because the urine on the urine absorbed sheet has surface tension.

BRIEF DESCRIPTION OF THE SEVERAL VIEWS OF THE DRAWINGS

FIGS. 1 through 6 are diagrams showing an embodiment of an automatic urine disposal device of the present invention.

DETAILED DESCRIPTION OF THE INVENTION

A urine receptacle for absorbing urine is attached to the urinating part of a device wearer. After being absorbed by the urine receiver, urine is directed into a sealed urine tank via a urine drainage tube. In the urine tank, a urine swaying motion control means is provided to control swaying motions or rippling motions of discharged urine. A vacuum pump suctions air inside the urine tank so that urine will be drawn into the urine tank. The urine receptacle has: a support sheet having no water permeability with a urine drainage pore to which the urine drainage tube is connected; a urine absorbing sheet, held by the support sheet, for absorbing urine; urine absorbing space forming material placed between the support sheet and the urine absorbing sheet; a urine backflow prevention sheet, placed between the urine absorbing sheet and the top sheet, with a plurality of funnel-shaped pores; and between the top sheet and the urine backflow prevention sheet a urine detection sensor with two rectangular electrodes which become electrically conductive when in contact with urine.

Figure 1:
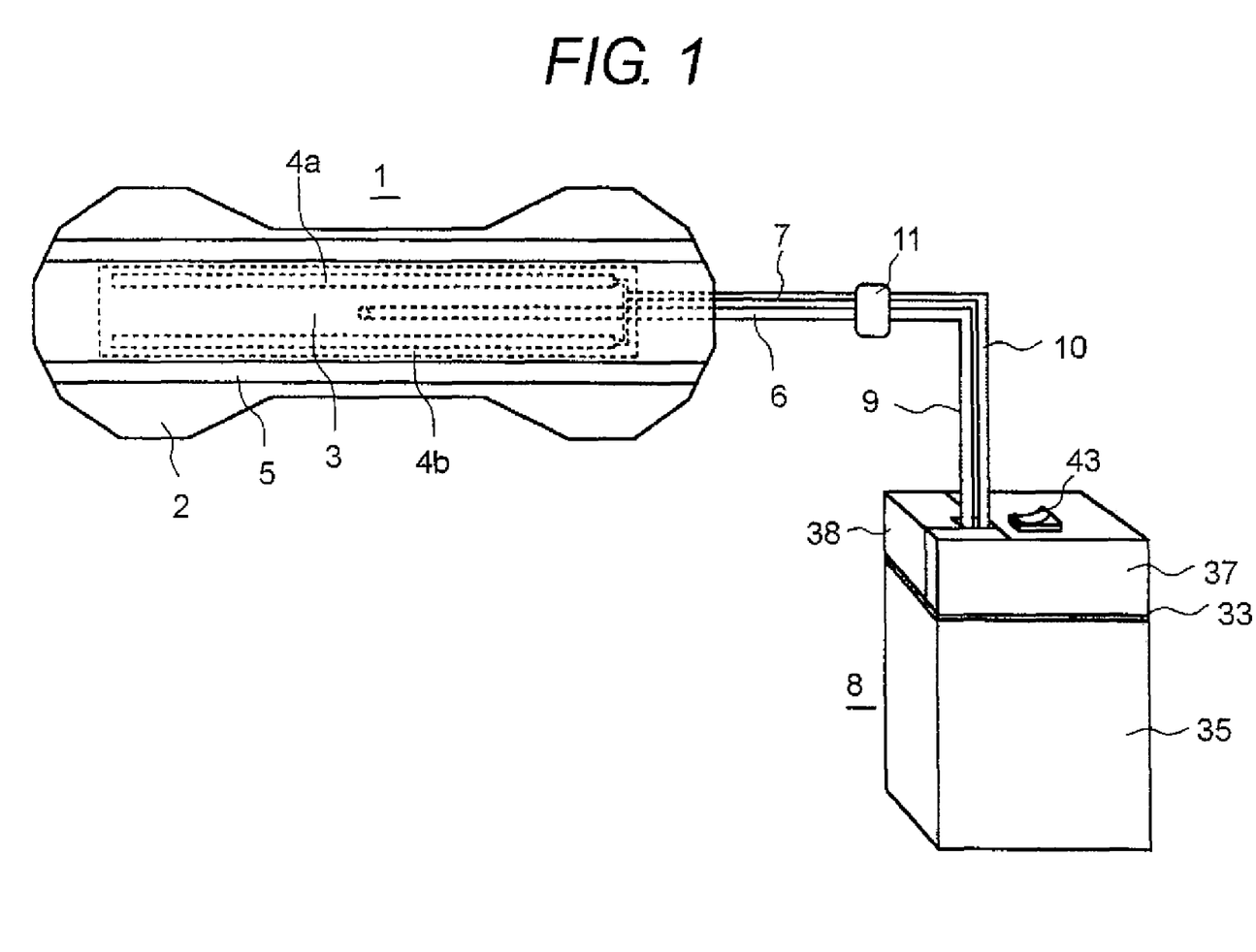
FIG. 1 is a perspective view of the entire device.
Figure 2:
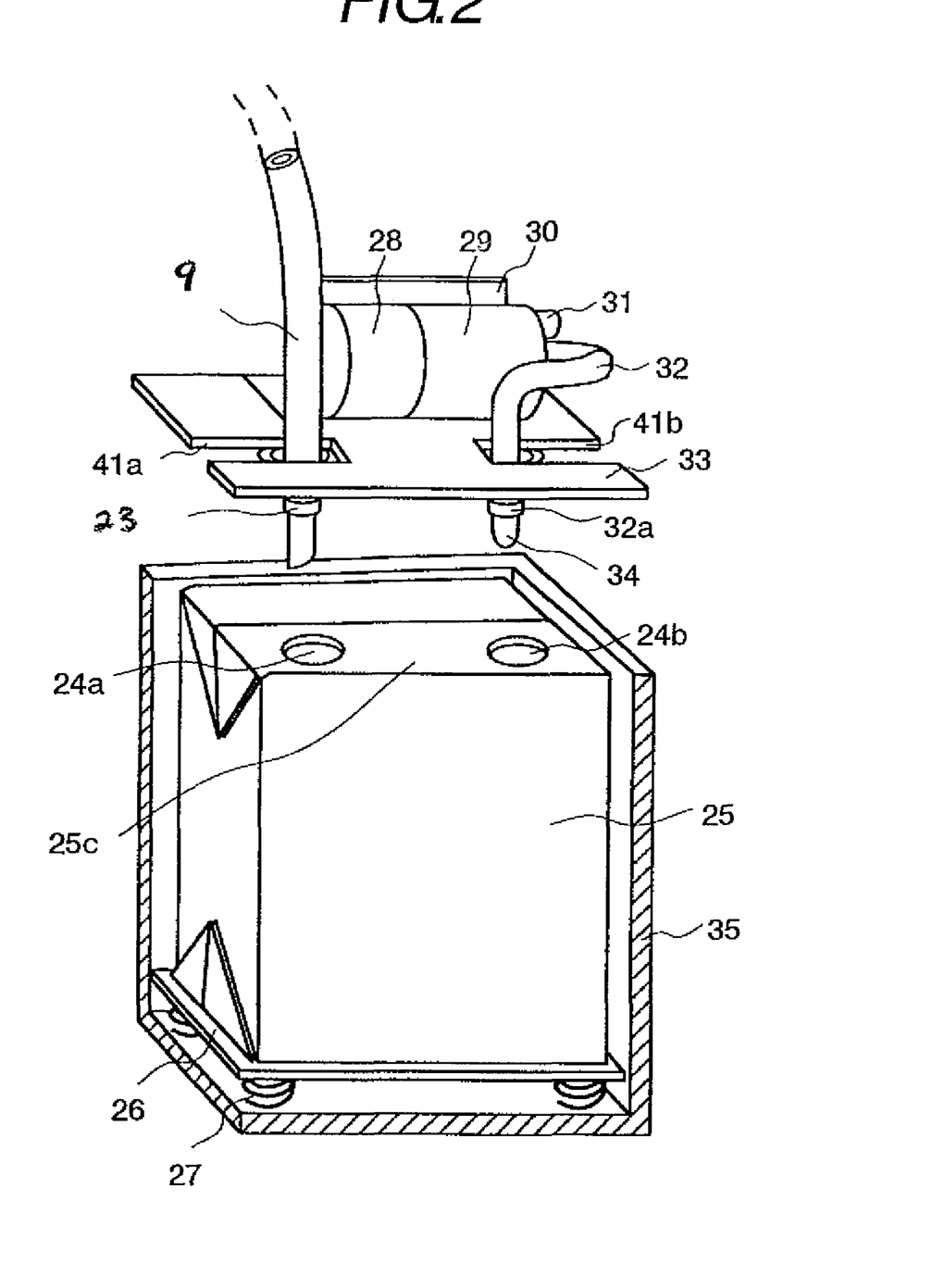
FIG. 2 is an exploded perspective view of the device with its urine tank partially removed and its lid case removed.
Figure 3:
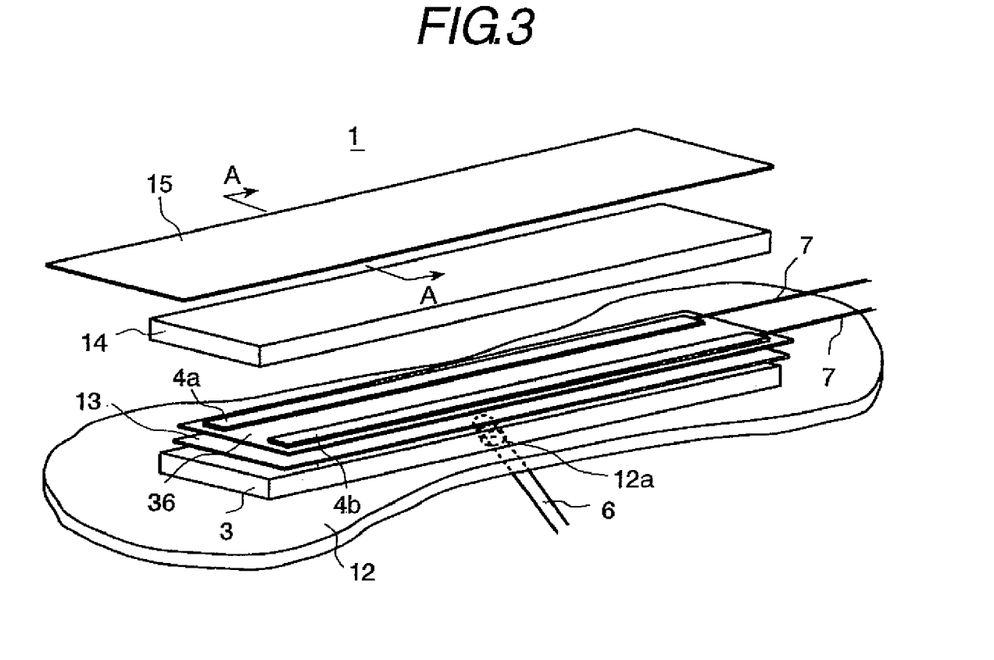
FIG. 3 is an exploded perspective view of a urine receptacle.
Figure 4:
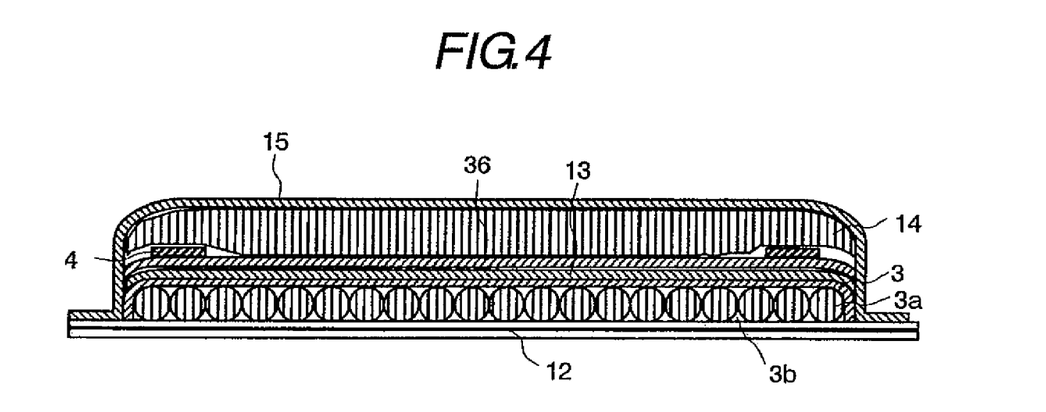
FIG. 4 is a cross-sectional view of the urine receptacle taken along the line A-A in FIG. 3.

FIGS. 1 through 4 are diagrams showing an embodiment of the present invention. FIG. 1 is a schematic diagram of an automatic urine disposal device of the present invention, FIG. 2 is an exploded perspective view of the device with its urine tank partially removed and its lid case removed, FIG. 3 is an exploded and enlarged perspective view of a urine receptacle, and FIG. 4 is an enlarged cross-sectional view of the urine receptacle taken along the line A-A in FIG. 3.

FIGS. 1 through 4 show an example in which a urine pack, as a urine storage container, is housed in the urine tank. Although a urine receptacle 1 is shown as a flat structure in these figures, it is in fact structured such that it concaves like a funnel on the surface that is in contact with the wearer's crotch, and its width at the middle in the longitudinal direction (direction of the wearer's front and rear) is narrower at the middle part as shown in FIGS. 1 and 3. The urine receptacle 1 is thus shaped like an hourglass so that it fits the wearer's crotch.

The urine receptacle shown in FIG. 1 is a view from the top, looking down the surface that comes in contact with the wearer's crotch. A urine absorbing sheet 3 for absorbing discharged urine and a urine detection sensor 4 (electrodes 4a and 4b) for detecting urination are placed inside the urine receptacle. Below the urine absorbing sheet 3, bead-shaped urine absorbing space forming material 3a is placed. A set of the urine absorbing sheet 3 and the urine absorbing space forming material 3a is sometimes collectively referred to as a urine collecting member 3.

On the urine receptacle 1, gathers 5 are formed. The gathers 5 have a three-dimensional structure for preventing urine from leaking from the sides. The urine collecting member 3 and the urine detection sensor 4 are structured so as to have a long length in the direction of the wearer's front and rear with his/her crotch at the middle in order to detect and collect discharged urine from a large area. A urine drainage tube 6 is connected to the middle part of the urine collecting member 3. A signal line 7 is connected to the urine detection sensor 4. Also, a urine drainage tube 9 and a signal line 10 are connected to the portable urine disposal device 8, and a joint 11 is connected to one end of the urine drainage tube 9 and one end of signal line 10.

The joint 11 is capable of linking the urine drainage tube 6 to the urine drainage tube 9, and the signal line 7 to the signal line 10 through a single operation. After using the urine receptacle 1 for a day or if it becomes dirty due to defecation, the urine receptacle 1 can be detached from the portable urine disposal device 8 from the joint 11 and discarded so that the wearer can wear a new urine receptacle 1.

As shown in FIG. 3, the urine receptacle 1 consists of a support sheet 12, the urine collecting member 3, a sheet 13 with funnel-shaped pores, the urine detection sensor 4, a cushion sheet 14, and a top sheet 15. The gathers 5 are made of a nonwoven fabric that does not let water through. The gathers 5 are shaped and arranged such that they stand along the longitudinal outline of the top sheet 15, tilting toward the inside, and are glued by a processing method such as the heat sealing method. The height of the gathers 5 is approximately 15 mm. These tilting gathers 4 prevent urine from leaking from the sides due to movement or weight shift of the wearer.

Figure 5:
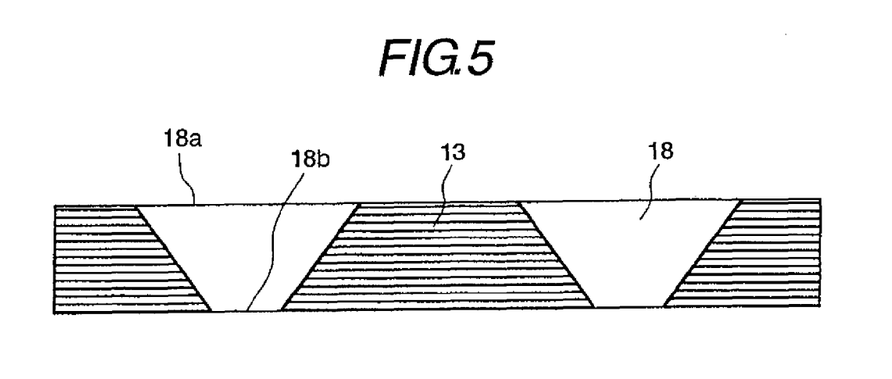
FIG. 5 is a partially enlarged view of a urine backflow prevention sheet.

The support sheet 12 is made of a flexible material such as a foamed polyethylene sheet. In the urine collecting member 3, consisting of the urine absorbing sheet and the urine absorbing space forming material 3a, a flow path 3b is formed as shown in FIG. 4, and this flow path 3b serves as small urine absorbing space for collecting urine. Also, a urine drainage pore 12a is formed on the support sheet 12, and the urine drainage tube 6 passes through this urine drainage pore 12a. The urine drainage tube 6 is made of soft, flexible materials such as soft resins. As seen in FIG. 5, a urine backflow prevention sheet 13 is formed by a polyethylene film with no water permeability having funnel-shaped pores 18.

The electrodes 4a and 4b, constituting the urine detection sensor 4, are glued and arranged such that they are parallel to an electrode support sheet 36. The electrode support sheet 36 with high water permeability is formed by a thin thermally bonded nonwoven fabric, and is placed between the urine backflow prevention sheet 13 and the cushion sheet 14. The cushion sheet 14 also has high water permeability and is formed by a thin thermally bonded nonwoven fabric. The cushion sheet 14 is made flexible so as to improve comfort for the wearer.

The top sheet 15 is formed by a thin thermally bonded nonwoven fabric having high water permeability. Since both the top sheet 15 and the cushion sheet 14 have high water permeability, discharged urine of the wearer can smoothly pass through these sheets and can be detected by the urine detection sensor 4. The cushion sheet 14 has a thickness of 3 to 5 mm to improve comfort for the wearer and to prevent discharged urine from returning to the skin of the wearer.

The top sheet 15 is designed as a mesh sheet having a thickness of approximately 1 mm to ensure high water and sweat absorbing rate. By allowing urine to rapidly reach to the cushion sheet 14 through small pores of the mesh sheet, the wearer will feel less dampness on his/her skin. The top sheet 15 is fixed so as to cover the cushion sheet 14, the urine detection sensor 4, the urine backflow prevention sheet 13, and the urine collecting member 3, and each side of the top sheet 15 is bonded to the support sheet 12. A processing method such as the heat sealing method is used to bond the top sheet 15 to the support sheet 12.

The support sheet has a length of approximately 320 mm (direction of the wearer's front and rear), maximum width of approximately 130 mm, minimum width of approximately 90 mm, and thickness of approximately 2 mm. The urine collecting member 3 has a length of approximately 250 mm (direction of the wearer's front and rear), width of approximately 45 mm, and thickness of approximately 10 mm. The urine backflow prevention sheet 13 and the cushion sheet 14 both have approximately the same length and width as that of the urine collecting member 3.

The portable urine disposal device 8 consists of a urine tank 35, a lid case 37, and a battery box 38. The urine tank 35 is made of resins and has the shape of a rectangular solid with an opening on the top. A spring 27 is located at each corner of the bottom plate of the urine tank 35 to provide elastic suspension to a support board 26. A urine pack 25 as a urine storage container is sealed with a sheet of heavy paper like that of a milk carton, and two tube guide holes 24a and 25b are formed on a top surface 25c of the urine pack 25. Although not shown, the urine pack 25 contains particulate superabsorbent polymers such as cross-link polyacrylic acid soda that become gelatinized after absorbing urine. The superabsorbent polymers provide a urine swaying motion control means that prohibits urine from swaying (rippling) inside the urine pack 25.

The urine pack 25 is made with, for example, a sheet of heavy paper like that of a milk carton, and is shaped like a rectangular solid. A partition plate (not shown) is placed inside the pack so that the pack can be resistant to vacuum pressure. Capacity of the urine pack 25 is approximately 500 ml, which is sufficient for storing two instances of urination. As a portable device, however, its dimensions can be adjusted to 110 mm×110 mm×50 mm (605 ml). Also, for longer usage times, such as clinical use or nighttime use, its capacity can be made 1000 ml or more. Note that the shape of the urine tank 35 and the urine pack 25 can be changed in order to fit them to the shape of the wearer's body.

A lid plate 33 is located on the top opening of the urine tank 35, and the lid case 37 is provided so as to cover the lid plate 33. In the space defined by the lid case 37 and lid plate 33, a vacuum pump 29 is placed. The vacuum pump 29 is driven by a motor 28. One end of a suction tube 32 and an air release tube 31 are linked to the vacuum pump 29. Just as with the urine drainage tubes 6 and 9, the suction tube 32 and the air release tube 31 are formed by soft, flexible materials.

The motor 28 uses the battery placed inside the battery box 38, shown in FIG. 1, as the driving power and is controlled by the controller mounted on a control board 30. The battery box 38 is installed in the lid case 37 like a cassette to supply power to the motor 28, and uses alkaline cells or secondary batteries. The size of the vacuum pump 29 is small; the diameter is approximately 30 mm or smaller, the length is approximately 70 mm or shorter, and the battery voltage is 5 to 9 V.

On the top surface of the lid case 37, a manual switch 43 for manually driving the motor 28 is provided. When the lid case 37 is fitted to the urine tank 35, a one-touch lock mechanism (not shown) locks them together. On the lid plate 33, a cutout section 41a for guiding the urine drainage tube 9 and another cutout section 41b for guiding the suction tube 32 are formed. Both the urine drainage tube 9 and the suction tube 32 have a diameter of approximately 5 mm, and the width of each of the cutout sections 41a and 41b is approximately 6 mm.

On the other end of the urine drainage tube 9, a mounting fixture 23 is attached for fixing the urine drainage tube 9 to the urine pack 25. An insertion hole is formed in the mounting fixture 23 for inserting and holding the urine drainage tube 9, and the mounting fixture 23 fixes the urine drainage tube 9 to the tube guide hole 24a to connect the urine drainage tube 9 to the urine pack 25 while maintaining the airtightness of the urine pack 25. The mounting fixture 23 has a funnel-like shape and is made of flexible materials made of soft resins, and can be detached from/attached to the tube guide hole 24a.

The funnel-shaped mounting fixture 23 has its outer surface and inner surface in the shape of a taper. For example, the mounting fixture 23 has a taper angle of 30 degrees from its axis, the largest diameter of the outer surface taper is 8.0 mm, and the smallest diameter is approximately 6.1 mm. As mentioned earlier, the width of the cutout section 41a on the lid plate 33 is approximately 6 mm. When the urine drainage tube 9 is guided into the cutout section 41a, the tube cannot be pulled upwards due to the mounting fixture 23, as seen in FIG. 2.

The mounting fixture 23 is inserted into the tube guide hole 24a formed on the top surface 25c of the urine pack 25 from the side with the smallest diameter (6.1 mm), while holding the inserted urine drainage tube 9. The diameter of the tube guide hole 24a is approximately 6.5 mm, which is somewhere between the largest and smallest diameters of the taper provided on the outer surface of the mounting fixture 23. When the mounting fixture 23 is fixed to the tube guide hole 24a, the urine pack 25 becomes sealed while maintaining its airtightness. The mounting fixture 23 is fitted to the tube guide hole 24a by insertion, and is configured to be detachable from/attachable to the tube guide hole 24a. The urine drainage tube 9 becomes connected to the urine pack 25 by the mounting fixture 23 becoming fitted to the tube guide hole 24a.

The suction tube 32 has one end linked to the vacuum pump 29, and a filter 34 is attached on the other end. The filter 34 serves to remove the odor, but it also prevents fluid that may spread in the urine pack 25 at the time of urine suction from being vacuumed into the vacuum pump 29.

A mounting fixture 32a is attached to the other side of the suction tube 32 to fix the suction tube 32 to the urine pack 25. This mounting fixture 32a is the same one as the mounting fixture 23 attached to the urine drainage tube 9. The mounting fixture 32a is fitted to the tube guide hole 24b by insertion, and is configured to be detachable from/attachable to the tube guide hole 24b. The mounting fixture 24a becomes fitted to the tube guide hole 24b while maintaining the airtightness of the urine pack 25.

FIG. 2 shows the urine drainage tube 9 with the mounting fixture 23 attached and the suction tube 32 with the mounting fixture 32a, guided and fitted into the cutout sections 41a and 41b respectively. While maintaining the tubes and the mounting fixtures in that state, the lid plate 33 and then the lid case 37 are placed on the top opening of the urine tank 35 as shown in FIG. 1. The ends of the urine drainage tube 9 and suction tube 32 are inserted into the tube guide holes 24a and 24b provided on the urine pack 25. The mounting fixtures 23 and 32a are pressed down below the cutout sections 41a and 41b provided on the lid plate 33, and the taper parts of the fixtures are inserted and glued to the tube guide holes 24a and 24b provided on the urine pack 25.

Meanwhile, the urine pack 25 is pressed upward by the support plate 26 elastically supported by the springs 27. This mechanism allows an increase in degree of adhesion between the mounting fixtures 23 and 32a, and the tube guide holes 24a and 24b provided on the urine pack 25. Note that, application of a soft material on the surface 25c of the urine pack 25 having the tube guide holes 24a and 24b can also improve the degree of adhesion between the mounting fixtures 23 and 32a, and the tube guide holes 24a and 24b.

Figure 6:
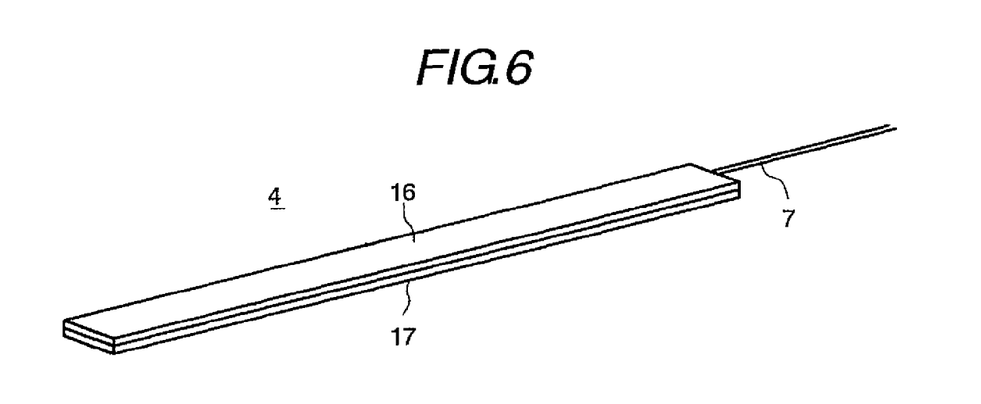
FIG. 6 is a perspective view of a urine detection sensor.

As shown in FIG. 6, the urine detection sensor (electrodes) has a conducting surface 16 and an insulating surface 17, and the signal line 7 is connected to this sensor. The insulating surface 17 side of the electrodes 4a and 4b (the urine detection sensor 4) is glued to the electrode support sheet 36. When urine is stored between the electrodes 4a and 4b, the conducting surface 16 becomes electrically conductive, and the sensor detects urination. Since the current generated between the electrodes 4a and 4b is approximately 0.1 mA and is thus extremely low, the electric current will have no impact on the wearer.

A urine detection signal from the urine detection sensor 4 is sent to a controller mounted on the control board 30 via the signal lines 7 and 10. The insulating surface 17 of the electrode 4 is made of an insulating material such as paper or vinyl. The conducting surface 16 is created by applying the aluminum evaporation method to the backside of the insulating surface 17. The urine detection sensor (electrodes) 4 has a length of approximately 200 mm, width of approximately 5 mm, and thickness of approximately 0.2 mm. The distance between the electrodes 4a and 4b, arranged in parallel with each other, is approximately 30 mm.

As the urine backflow prevention sheet 13, a plurality of minute funnel-shaped pores 18 are formed on a polyethylene film as seen in FIG. 5, and each pore has a large top area and a small bottom area. Urine discharged onto the top sheet 15 enters a top opening 18a of the funnel-shaped pore 18 formed on the urine backflow prevention sheet 13, and gets absorbed by the urine collecting member 3.

Some urine remains uncollected in the flow path 3b or other space inside the urine collecting member 3 due to surface tension of the urine. If a weight shift caused by the wearer changing his/her posture gives some kind of physical impact on the urine collecting member 3, the residual urine goes back to the urine detection sensor 4. Making the area of a bottom opening 18b of the funnel-shaped pore 18 small makes it difficult for urine to flow back. For example, the diameter of the top opening 18a of each funnel-shaped pore 18 is 1 to 2 mm, the diameter of the bottom opening 18b of each funnel-shaped pore 18 is 0.5 to 1 mm, and the funnel-shaped pores 18 are arranged with a 3 to 5 mm interval.

Note that, it is desirable that a surface acting agent be applied to or woven into the urine backflow prevention sheet 13 such that surface tension becomes reduced and discharged urine will smoothly flow from the top surface to the bottom surface. Also, pores on the urine backflow prevention sheet 13 can be formed by a method such as the perforation method. In the perforation method, the sheet 13 is placed between jigs of a pore forming plate and a mesh plate, and hot air is blown at the pore forming plate and is suctioned from the mesh plate side, creating pores.

In this configuration, the urine receptacle 1 is attached to the wearer (not shown) such that it touches his/her urinating part inside the underwear. The portable urine disposal device 8 including the lid case 37 containing the urine tank 35, vacuum pump 29, and motor 28 will be carried around by the wearer, or is placed on or under the bed when the wearer is lying on a bed.

When the wearer urinates with the device placed in the manner described above, discharged urine flows into the urine detection sensor 4 after passing through the top sheet 15 and the cushion sheet 14. Urine then passes through the urine backflow prevention sheet 13 and becomes absorbed by the urine collecting member 3. When the space between the electrodes 4a and 4b of the urine detection sensor 4 is filled with urine, the conducting surface 16 becomes electrically conductive. The urine detection signal from the urine detection sensor 4 is then sent to the controller mounted on the control board 30 via the signal lines 7 and 10.

The controller mounted on the control board 30 activates the motor 28 and then drives the vacuum pump 29. When the vacuum pump 29 is activated, air pressure inside the urine pack 25 becomes lower due to air release, creating negative pressure in the urine drainage port 12a of the urine receptacle 1. When negative pressure is created in the urine drainage port 12a, urine absorbed by the urine collecting member 3 of the urine receptacle 1 is efficiently vacuumed by the urine drainage tube 6 due to suction power generated by negative pressure. Urine, vacuumed by the urine drainage tube 6, is then drawn by negative pressure into the urine pack 25 via the urine drainage tube 9 and is then stored therein.

Note that, upon urinating, the wearer can use the manual switch 43 to activate the motor 28 to draw the urine into the urine pack 25.

Urine, drawn into the urine pack 25, then has chemical reactions with particulate superabsorbent polymers (not shown) and becomes gelatinized. Gelatinization of the urine can prevent the swaying (rippling) motion of the urine inside the urine pack 25. Therefore, it is possible to configure a portable automatic urine disposal device in a preferred form, in which urine will not leak even if it is carried around.

When urination by the wearer finishes and the urine detection signal from the urine sensor 4 is no longer sent out, the controller mounted on the control board 30 stops the motor 28 and then stops the vacuum pump 29. It is also possible to stop the motor 28 and vacuum pump 29 by using the manual switch 43. If the urine pack 25 has sufficient capacity for holding two-times-worth of urine, the next urination process is conducted in the same manner.

After urine is stored in the urine pack 25, the urine pack 25 must be discarded by first unlocking the lock mechanism (not shown) to separate the urine tank 35 and the lid case 37, and then by removing the mounting fixtures 23 and 32a from the urine pack 25. The urine pack 25 is made of paper and thus can be disposed of as burnable waste.

After using the urine receptacle 1 for a day or if it becomes dirty due to defecation, the urine receptacle 1 must be discarded and replaced with a new urine receptacle 1 by disconnecting the urine drainage tubes 6 and 9 as well as the signal lines 7 and 10 from the one-touch joint 11. The urine receptacle 1 can be disposed of as burnable waste.

From a hygiene standpoint, the urine drainage tube 9 must be replaced after one or two days of use. Replacement of the urine drainage tube 9 can be done by disconnecting the urine drainage tubes 6 and 9 as well as the signal lines 7 and 10 from the one-touch joint 11. Then, after separating the urine tank 35 and the lid case 37, the mounting fixture 23 must be removed from the tube guide hole 24a on the urine pack 25 as shown in FIG. 2. The mounting fixture 23 can be easily removed by grabbing the mounting fixture 23 and pulling it out from the tube guide hole 24a. Replacement of the urine drainage tube 9 can be done easily as well as cleanly.

The drainage tube 9 must then be removed from the cutout section 41a and disposed of with the mounting fixture 23, followed by installation of a new urine drainage tube 9 into the tube guide hole 24a provided on the urine pack 25.

Note that air leakage of the suction tube 32 can be examined in the same manner as replacement of the urine drainage tube 9.

Urine discharged by the wearer can be thus disposed of, and backflow of urine to the urine detection sensor 4 can be prevented even if a weight shift by the wearer causes physical impact on the urine collecting member 3 since the present invention uses the urine backflow prevention sheet 13 with no water permeability. Although there is the possibility that urine comes in contact with the urine detection sensor 4 through the funnel-shaped pore 18 on the urine backflow prevention sheet 13 provided immediately below the urine detection sensor 4, the sensor will not operate improperly since the bottom surface of the urine detection sensor 4 (the electrodes 4a and 4b) is designed as the insulating surface 17.

For such urine disposal as described above, the urine detection sensor with a plurality of funnel-shaped pores is placed on top of the urine backflow sheet (on the top sheet side). Discharged urine can easily flow from the top sheet to the urine absorbing sheet since each funnel-shaped pore has a large opening area at the top, and discharged urine cannot backflow easily as each funnel-shaped pore has a small opening area at the bottom. This is because the urine on the urine absorbed sheet has surface tension. Therefore, even though a urine detection sensor with a pair of electrodes is used, it is possible to prevent incorrect operation of the vacuum pump caused by residual urine and also the wearer can use the device comfortably.

Note that, while urine is directed into the urine pack contained inside the urine tank in the embodiment described above, it is clear that it is also possible to seal the urine tank with the lid, form a tube guide hole on the lid, and attach the urine drainage tube to the hole. In this case, the other end of the suction tube can be fixed and linked to the urine tank.

Figure 7:
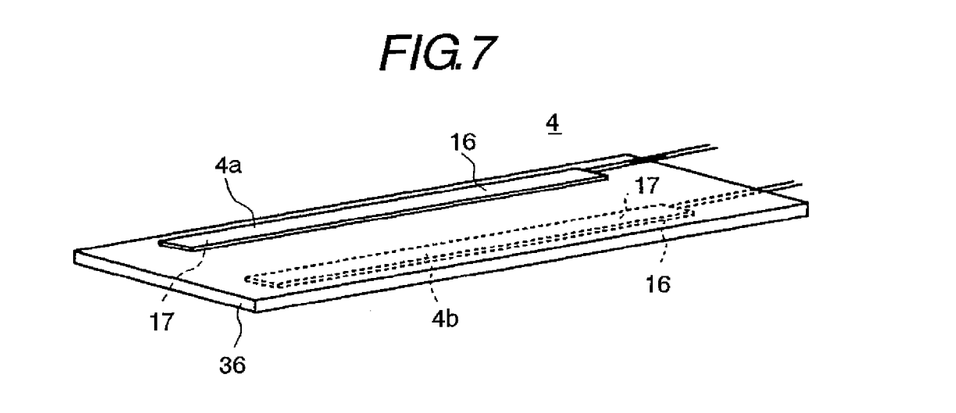
FIG. 7 through 9 are diagrams showing perspective views of the urine detection sensor of another embodiment of the present invention.
Figure 8:
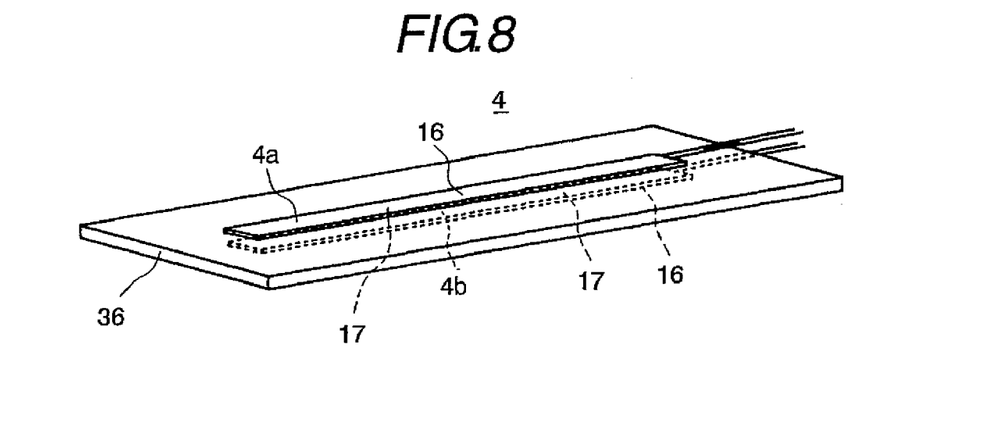
Figure 9:
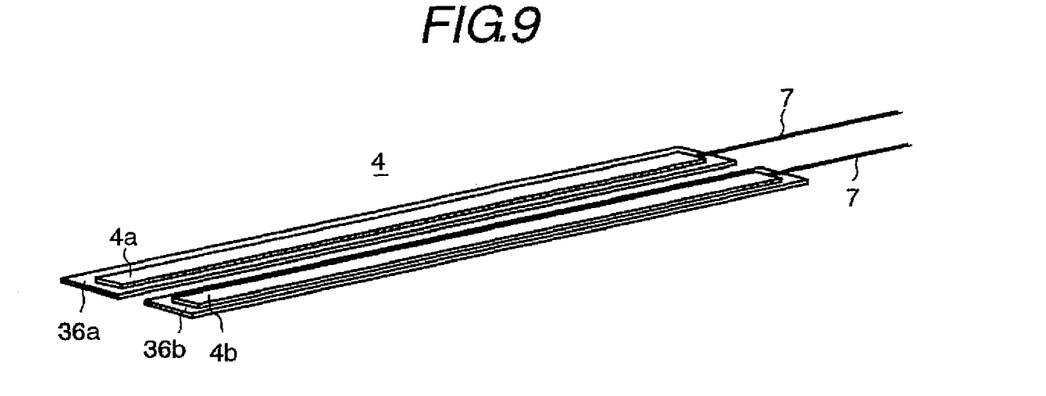

FIGS. 7 through 9 show other examples of the urine detection sensor 4.

FIG. 7 shows the rectangular electrode 4a glued on one side of the electrode support sheet 36 and the rectangular electrode 4b glued on the other side of the electrode support sheet 36. The insulating surface 17 of the electrodes 4a and 4b is glued onto the electrode support sheet 36. The urine detection sensor 4 shown in FIG. 7 is also capable of correct urine detection.

FIG. 8 shows the rectangular electrode 4a glued on one side of the electrode support sheet 36 and the rectangular electrode 4b glued on the other side of the electrode support sheet 36, but in this example, the electrodes are glued at the same locations with the sheet in between. The insulating surface 17 of the electrodes 4a and 4b is glued onto the electrode support sheet 36. The urine detection sensor 4 shown in FIG. 8 is also capable of correct urine detection.

FIG. 9 shows the electrode support sheet 36, with the rectangular electrodes 4a and 4b glued on, divided into electrode support sheets 36a and 36b. The insulating surface 17 of the electrodes 4a and 4b is glued onto the electrode support sheets 36a and 36b. The urine detection sensor 4 shown in FIG. 9 is also capable of correct urine detection. Also note that incorrect operation of the urine detection sensor 4 can be prevented even if the electrode support sheets 36a and 36b contain moisture.

As described above, in the present invention, a urine detection sensor is placed on (the top sheet side of) a urine backflow prevention sheet having a plurality of funnel-shaped pores. Since this configuration is capable of inhibiting urine from flowing back, it is possible to prevent incorrect operation of a vacuum pump caused by residual urine even though a urine detection sensor having a pair of electrodes is used. Such configuration will allow the wearer to use the device comfortably.

Therefore, the device of the present invention is capable of preventing incorrect operation of a vacuum pump caused by residual urine even though a urine detection sensor having a pair of electrodes is used and can be comfortably used by its wearer.

The preferred embodiment described herein are therefore illustrative and not restrictive, the scope of the invention being indicated by the appended claims and all variations which come within the meaning of the claims are intended to be embraced therein.

What is claimed is:

1. A urine receptacle for absorbing urine discharged from the urinating part of a wearer, to be used with an automatic urine disposal device, comprising:
   a support sheet with a urine drainage port formed thereon, the support sheet having no water permeability,
   a urine absorbing sheet for absorbing urine held by said support sheet,
   a urine absorbing space forming material placed between said support sheet and said urine absorbing sheet,
   a urine backflow prevention sheet with funnel-shaped pores, the urine backflow prevention sheet being located between said urine absorbing sheet and a top sheet, and
   a urine detection sensor having two electrodes, the urine detection sensor being placed between said top sheet and said urine backflow prevention sheet.

2. The urine receptacle according to claim 1, characterized in that
   a plurality of funnel-shaped pores are formed on said urine backflow prevention sheet, and
   said electrodes are rectangular-shaped.

3. A urine receptacle for absorbing urine discharged from the urinating part of a wearer, to be used with an automatic urine disposal device, comprising:
   a support sheet with a urine drainage port formed thereon, the support sheet having no water permeability,
   a urine absorbing sheet for absorbing urine held by said support sheet,
   a urine backflow prevention sheet with funnel-shaped pores, the urine backflow prevention sheet being located between said urine absorbing sheet and a top sheet,
   a cushion sheet placed between said top sheet and said urine backflow prevention sheet, and
   a urine detection sensor having two electrodes, the urine detection sensor being placed between said top sheet and said urine backflow prevention sheet, wherein
   said electrodes are placed between the cushion sheet and said urine backflow prevention sheet.

4. An automatic urine disposal device, comprising:
   a urine receptacle for absorbing urine discharged by a wearer,
   a sealed urine tank for storing urine collected by the urine receptacle, and
   a urine drainage tube for directing urine from the urine receptacle into the urine tank, characterized in that,
   a vacuum pump for lowering pressure inside said urine tank is provided, and
   said urine receptacle has a water impermeable flexible support sheet to which said urine drainage tube is connected, a water permeable top sheet, a urine absorbing sheet for absorbing urine that has passed through said top sheet, said urine absorbing sheet being supported on said support sheet, a urine backflow prevention sheet placed between said top sheet and said urine absorbing sheet, a urine detection sensor with a pair of electrodes placed between said top sheet and said urine backflow prevention sheet, said urine detection sensor having an insulating layer on the bottom face thereof, a bead-shaped forming material placed on the support sheet side of said urine absorbing sheet, and a water permeable cushion sheet placed between said top sheet and said urine detection sensor,
   wherein urine discharged from the wearer flows into said urine detection sensor through said top sheet and said cushion sheet bringing said urine detection sensor to an electrically conductive state as a signal of the urine detection with said vacuum pump activated, and said vacuum pump stops when the signal of the urine detection ceases on the end of urination.

5. The automatic urine disposal device according to claim 4, characterized in that said urine backflow prevention sheet has a plurality of pores.

6. The automatic urine disposal device according to claim 4, characterized in that said electrodes are placed on a water permeable electrode support sheet in parallel thereto and bonded thereon.

7. A urine receptacle for absorbing urine discharged from the urinating part of a wearer using a vacuum pump, said urine receptacle to be used with an automatic urine disposal device, comprising:

a water impermeable flexible support sheet to which a urine drainage tube is connected, a water permeable top sheet, a urine absorbing sheet for absorbing urine that has passed through said top sheet, said urine absorbing sheet being supported on said support sheet, a urine backflow prevention sheet placed between the top sheet and the urine absorbing sheet, a urine detection sensor with a pair of electrodes placed between said top sheet and said urine backflow prevention sheet, said urine detection sensor having an insulating layer on the bottom thereof, a urine absorbing space forming material placed on the support sheet side of said urine absorbing sheet, and a water permeable cushion sheet placed between said top sheet and said urine detection sensor, wherein urine discharged from the wearer flows into said urine detection sensor through said top sheet and said cushion sheet bring said urine detection sensor to an electrically conductive state as a signal of the urine detection with said vacuum pump activated, and said vacuum pump stops when the signal of the urine detection ceases on the end of urination.

8. The urine receptacle according to claim 7, characterized in that said urine backflow prevention sheet has a plurality of pores.

9. The urine receptacle according to claim 7, characterized in that said electrodes are placed on a water permeable electrode support sheet in parallel thereto and bonded thereon.

* * * * *